United States Patent
Tran et al.

(10) Patent No.: US 7,332,722 B1
(45) Date of Patent: Feb. 19, 2008

(54) SIMULTANEOUS MULTI-HEADED IMAGER GEOMETRY CALIBRATION METHOD

(75) Inventors: Vi-Hoa Tran, Newport News, VA (US); Steven Richard Meikle, Penshurst (AU); Mark Frederick Smith, Yorktown, VA (US)

(73) Assignee: Jefferson Science Associates, LLC, Newport News, VA (US)

( * ) Notice: Subject to any disclaimer, the term of this patent is extended or adjusted under 35 U.S.C. 154(b) by 0 days.

(21) Appl. No.: 11/358,270

(22) Filed: Feb. 21, 2006

(51) Int. Cl.
*G01T 1/161* (2006.01)
(52) U.S. Cl. .................................... 250/363.09
(58) Field of Classification Search ............ 250/363.09
See application file for complete search history.

(56) References Cited

U.S. PATENT DOCUMENTS

| | | | | |
|---|---|---|---|---|
| 5,036,530 A | * | 7/1991 | DiGiovanna et al. ....... | 378/208 |
| 6,137,109 A | * | 10/2000 | Hayes .................... | 250/363.05 |
| 2007/0029491 A1 | * | 2/2007 | Olden et al. ........... | 250/370.08 |

OTHER PUBLICATIONS

Characterization of Pinhole SPECT Acquisition Geometry, Beque et sl., Medical Imaging, IEEE Transactions, vol. 22, pp. 599-612, 2003.
A. G. Weisenberger, et al. Development and Testing of a restraint Free Small Animal SPECT Imaging System with Infrared Based Motion Tracking, NSS Conference Record, IEEE, 2003.
J.S. Goddard, et al., Real Time Landmark-based unrestrained Tracking System for Motion-Corrected PET/SPECT Imaging, NSS Conference Record, IEEE, 2002.
Beque et al., Optimization of Pinhole SPECT Calibration; presented at Nuclear Science Symposium Conference Record, IEEE, 2003.

* cited by examiner

*Primary Examiner*—David Porta
*Assistant Examiner*—Marcus H Taningco

(57) ABSTRACT

A method for calibrating multi-headed high sensitivity and high spatial resolution dynamic imaging systems, especially those useful in the acquisition of tomographic images of small animals. The method of the present invention comprises: simultaneously calibrating two or more detectors to the same coordinate system; and functionally correcting for unwanted detector movement due to gantry flexing.

4 Claims, 13 Drawing Sheets

US 7,332,722 B1

SIMULTANEOUS MULTI-HEADED IMAGER GEOMETRY CALIBRATION METHOD

The United States of America may have certain rights to this invention under Management and Operating Contract No. DE-AC05-84ER 40150 from the Department of Energy.

FIELD OF THE INVENTION

The present invention relates to the SPECT imaging of small animals and more particularly to calibration methods useful for obtaining high resolution, high efficiency dynamic images of small animals injected with a biomarker.

BACKGROUND OF THE INVENTION

Single Photon Emission Computed Tomography (SPECT) as a form of nuclear medicine imaging is used to show how organs, systems and different molecular processes in the human body are functioning. Acquisition of 3d SPECT images takes about 20-40 minutes, depending on procedure, and during this time it is usually assumed that the 'function' that is being imaged is stationary, not changing in time during the duration of the scan. During the SPECT scan the 1 to 3 imaging detector heads are rotating slowly around the patient recording views of the patient's body or organs from different angles. This is how the tomographic information is collected to reconstruct later the patient images in 2d views-slices through the 3d reconstructions. However, most of the body functions are dynamic and this leads to the loss of this important dynamic information and even to errors (artifacts) showing up in the reconstructed images. In some studies this dynamic 3d information is crucial to the study and it often prevents the use of SPECT in some important biological research and forces the researchers to move to Positron Emission Tomography (PET), where the imaging is acquired by a ring of many small stationary detectors. The basic principle of PET imaging combined with the relatively large, compared to SPECT, number of imaging modules provides sufficient number of viewing tomographic angles to produce high quality 3d reconstructions. However, PET technique requires development of special positron imaging agents while most of the existing agents are of a single photon type, applicable to SPECT. Therefore, there is a strong motivation to remedy this traditional limitation of the standard SPECT with few and slowly rotating detector heads. First, new reconstruction techniques have been developed which allow the generation of dynamic images from a normal clinical data acquisition. However, these techniques require complicated system modeling and assumptions about the dynamic processes that are to be unfolded in 3d reconstructions from the limited dynamic angular data obtained in a normal clinical acquisition with a slowly rotating gamma cameras.

In an effort to avoid these approximations, stationary brain SPECT systems were designed with a relatively large (12-24) number of detector heads compared to the standard SPECT, but still small compared to the optimal number of angular projections required in an artifact-free high resolution SPECT. To increase the number of available simultaneous projections, some of these stationary SPECT designs use multiple pinhole collimators. In some designs, the collimators are rotating to increase the number of projections. However, these special clinical SPECT systems are at present only limited to imaging the brain.

High resolution SPECT molecular imaging of small animals such as mice and rats used in models of many human diseases, typically requires that even more planar images are acquired by stepping a few (sometimes as little as one to three) imaging detector heads around the animal. Such scans may consist of over a 100 individual images or projections obtained by stepping a rotating gantry by the same angular increment of an order of a few degrees and acquiring an image typically for 5-20 seconds. This is called a step-and-shoot mode of scanning. In other scans imaging heads are permitted to continuously and slowly rotate about the object and the individual images-projections are obtained by combining collected data from a range of viewing angles falling within an angle increment. Independently of the version of this type of a scan with a slow rotation speed of the imaging heads, a high a number of different angular views of the object-animal with distributed gamma activity is necessary to obtain high quality, artifact-free 3d reconstructions of the activity distributions (uptakes) in the animal organs, in tumors, etc. Typically the full rotation scanning procedure over 360 degrees takes from 20-60 minutes, or even longer. After the scan (involving at most one rotation only) is complete, the individual images-projections obtained for each stepping angle are read into a proper 3d reconstruction algorithm and results are presented in the form of 2d slices—planar cuts through the object-animal.

The most relevant prior art is the stationary ring SPECT system designed for small animals at the University of Arizona (1) Barrett et al. High-Resolution Imaging with 99 mTc-Glucarate for Assessing Myocardial Injury in Rat Heart Models Exposed to Different Durations of Ischemia with Reperfusion, Z. Liu, H. H. Barrett, G. D. Stevenson, G. A. Kastis, M. Bettan, L. R. Furenlid, D. W. Wilson, and K. Y. Pak, J. Nucl. Med., Jul. 1, 2004; 45(7): 1251-1259; 2) Imaging recognition of multidrug resistance in human breast tumors using 99m Tc-labeled monocationic agents and a high-resolution stationary SPECT system Zhonglin Liu*, Gail D. Stevenson, Harrison H. Barrett, George A. Kastis, Michael Bettan, Lars R. Furenlid, Donald W. Wilson, James M. Woolfenden, Nuclear Medicine and Biology 31 (2004) 53-65 www.elsevier.com/locate/nucmedbio; and 3) FastSPECT II: A Second-Generation High-Resolution Dynamic SPECT Imager, Lars R. Furenlid, Donald W. Wilson, Yi-chun Chen, Hyunki Kim, Philip J. Pietraski, Michael J. Crawford, and Harrison H. Barrett, IEEE TRANSACTIONS ON NUCLEAR SCIENCE, VOL. 51, NO. 3, June 2004, 631) based on a modified stationary brain SPECT (A stationary hemispherical SPECT imager for three-dimensional brain imaging, R K Rowe, J N Aarsvold, H H Barrett, J C Chen, W P Klein, B A Moore, I W Pang, D D Patton and T A White, Journal of Nuclear Medicine, Vol 34, 1993, Issue 3, 474-480). The motivation for that system was similar to the system described herein, but with even more strict requirements for fast temporary performance of under 1 second to enable dynamic cardiac imaging. However, because that stationary system is composed of a fixed number (16) of imaging modules, only the angular sampling accuracy of much less than the desired more than 100 samplings per 360 deg (3 deg or less per angular increment) is possible. This leads to problems with image reconstruction, such as artifacts, as mentioned above.

Another important difference between that rather large stationary system and the compact dynamic system described here is that to obtain high spatial resolution performance, the Arizona imager is equipped with pinhole collimators attached to larger imaging heads with moderate intrinsic spatial resolution. The detector heads are operating at a magnification factor of ~3 to compensate for their moderate intrinsic spatial resolution. In this way, the useful field-of-view is highly reduced and limited (by design) to primarily accurately image animal organs, such as the brain, heart, etc, and only a whole small mouse can be imaged. Therefore, that system cannot provide a dynamic image of a larger whole rodent animal such as a rat. In addition to the fixed size issue, the stationary SPECT design of Barrett et al uses few pinholes (one per module) and therefore cannot be optimized for high efficiency. Using pinhole collimators was not only necessary to achieve high spatial resolution, but it was also the only practical way to place 16 detector heads on a (large diameter) ring to provide the 16 independent views-projections. In our parallel-hole close geometry configuration it would not be possible to place even that small a number of modules on a ring and close to an animal. As explained before, the close detector distance to the object-animal is absolutely necessary to obtain the best possible combination of system spatial resolution and sensitivity, when using parallel-hole collimators.

As the quality of SPECT reconstruction depends on the number of independent views-projections and also in a crucial way on event statistics through detection efficiency (or on signal to noise ratio), the obtained images by the Arizona scanner indeed show the effects of limits in these two parameters.

Very high resolution stationary animal SPECT to image small objects such as a brain of a mouse, was proposed recently by Beekman et al (Design and simulation of a high-resolution stationary SPECT system for small animals, Freek J Beekman 1, 2 and Brendan Vastenhouw 1, 2, Phys. Med. Biol. 49 (2004) 4579-4592 PH: S0031-9155(04) 80035-6) by combining very high resolution pinhole imaging with large number of pinholes and with compact high-resolution gamma cameras. The system described herein solves the problem of the limited sensitivity-resolution trade-off that hampers contemporary small animal SPECT. One of the proposed designs, U-SPECT-III, uses a set of 15 detectors placed in a polygonal configuration and a cylindrical collimator that contains 135 pinholes arranged in nine rings. Each ring contains 15 gold pinhole apertures that focus on the center of the cylinder. A non-overlapping projection is acquired via each pinhole.

High-resolution scintillation detectors can be built based on angled columnar CsI(Tl) scintillator in such a way that it would eliminate the depth-of-interaction problem encountered with pinhole cameras. The expected intrinsic detector resolution is better than 150 μm. While this stationary SPECT design is theoretically optimized for very high sub-mm spatial resolution and high efficiency by using multi-pinhole collimator system, by design it covers only a small field of view (FOV) such as a brain of a mouse or a rat. This complicated concept cannot be easily adapted to a larger FOV such as a whole rat, or even a mouse.

In addition to the above dedicated animal SPECT efforts, the basis for several other attempts to build a dynamic small animal SPECT was the prior art related to the dynamic brain SPECT.

A stationary annular NaI(Tl) crystal and a rotating collimator system was for example used many years ago in a dedicated brain-imaging instrument (Radionuclide Annular Single Crystal Scintillator Camera with Rotating Collimator, S. Genna and S.-C. Pang, U.S. Pat. No. 4,584,478, Apr. 22, 1986; Genna S and Smith A P. The development of ASPECT, an annular single crystal brain camera for high efficiency SPECT. IEEE Trans Nucl Sci. 1988; NS-35: p. 654-658; and Holman B L, Carvalho P A, et al. Brain perfusion SPECT using an annular single crystal camera: initial clinical experience. J Nucl Med. 1990; 31: p. 1456-1461). More recently, a human "super rapid dynamic SPECT" (CERASPECT a brain-dedicated SPECT system. Performance evaluation and comparison with the rotating gamma camera, F Zito et al 1993 *Phys. Med. Biol.* 38 1433-1442) was further developed to make it even faster and used to evaluate retention process of 99 mTc-ECD in ischemic lesions (Development of super rapid dynamic SPECT, and analysis of 99 mTc-ECD dynamics as determined in ischemic lesion, Komatani A, Sugai Y, Hosoya T, Eur J Nucl Med 2001; 28 (Suppl): S1223, and Development of "super rapid dynamic SPECT," and analysis of retention process of 99 mTc-ECD in ischemic lesions: Comparative study with 133Xe SPECT, Akio KOMATANI, Yukio SUGAI and Takaaki HOSOYA, Annals of Nuclear Medicine Vol. 18, No. 6, 489-494, 2004). This stationary system is built as a ring of 21 scintillation modules, each made with three PMTs, attached to a continuous cylindrical scintillator gamma sensor. The patient's head is inserted in the cylindrical opening of the imager. The system is equipped with special high efficiency parallel hole collimators, one per each scintillation detection head. Time bins for dynamic tomographic projections as short as 2 sec are possible with this system. While offering good dynamic performance for the above clinical applications on human subjects, the system does not exhibit high enough spatial resolution to be used on small animals.

Focusing type collimators are used in another new dedicated Neurofocus Scanned Focal Point scanner (SFP™) brain imager (EVALUATION OF THE HIGH RESOLUTION NEUROFOCUS SPECT DEVICE FOR SMALL ANIMAL IMAGING, J. P. Seibyl, H. A. Stoddart, D. Martin, E. Smith, G. Wisniewski and H. F. Stoddart, Institute for Neurodegenerative Disorders, New Haven, Conn. and NeuroPhysics Corp, Shirley, Mass.). produced by Neurophysics Corporation. Twelve modules of this stationary ring SPECT cover axial FOV of 20 cm and are equipped with diverging collimators. As a result, spatial resolution on the central axis is only 3 mm FWHM, which is only marginally applicable to small animal imaging.

Nevertheless, several groups modified the human brain SPECT systems to adapt them for small animal imaging, sometimes with the dynamic imaging in mind.

An NIH group Green et al, (A NOVEL MOUSE SPECT SCANNER USING AN ANNULAR SCINTILLATION CAMERA, D. W. Jones*, A. L. Goertzen†, S. Riboldi†, J. Seidel†, K. Li‡, M. V. Green†, *Abstracts of the AMI Annual Meeting* 2003 109; and First Results from the High-Resolution mouse SPECT Annular Scintillation Camera. L. Goertzen 1, 2, D. W. Jones 3, J. Seidell, K. Lil, M. V. Green†, presented at the 2004 IEEE Medical Imaging Conference, Rome, 2004) modified a CERASPECT annular camera brain imager for small animal imaging by adding rotating pinhole collimators. This modified imager offering the possibility of dynamical SPECT imaging and dual tracer SPECT studies, is called mouseSPECT and uses collimator array comprised of eight equally spaced tungsten pinholes that continuously rotate around the prone and stationary animal at up to 1 rev/10 s. The pinholes simultaneously project eight non-overlapping images onto the annular scintillation crystal of a scanner. While the primary intention of that design was an 8-fold increase in sensitivity compared to a single rotating gamma camera with the same type single pinhole collimation, the relevant feature of that scanner is its ability to quickly capture a full 360 deg projection set of the object (animal) necessary to achieve 3d dynamic reconstructions.

The individual projection images from the pinholes are formed on the 31 cm diameter by 13 cm wide solid NaI(Tl) scintillator annulus. The intrinsic resolution of the imager (@140 keV) is 3.5 mm FWHM. The magnification geometry of the object-collimator-detector is so adjusted as to define the transaxial field of view of about 25 mm to allow imaging of a mouse. The 28 mm pinhole radius of rotation and the annular radius of the scanner combine to give a magnification of approximately 4.5. 0.5 mm and 1.0 mm diameter interchangeable pinhole inserts were used to allow a tradeoff between resolution and sensitivity depending on study requirements. Data is currently acquired in step-and-shoot mode, however the system is capable of list mode acquisition with the collimator continuously rotating. Images are reconstructed using a cone-beam OSEM method. The reconstructed spatial resolution of the system is 1.7 mm and the sensitivity at the centre of the FOV is 13.8 cps/microCi.

The above mentioned NeuroFocus brain imager was also tested for small animal imaging. The NeuroFocus is a high efficiency brain-dedicated stationary single photon imaging device utilizing 12 scanning detector heads fitted with 1 inch NaI crystals and 800 hole focused collimators with the potential for use in small animal imaging based on ultrahigh resolution while maintaining high count rate response. Measurements of the FWHM of the line spread function were determined for 99 mTc to be about 3 mm FWHM in the center of the field of view, which is marginal for imaging mice, but sufficient for many rat studies.

Non-orbiting tomographic system was proposed by Mosaic Imaging Technology (Non-orbiting tomographic imaging system, DeVito; Raymond P. (Palatine, Ill.); Haines; Edward J. (Marengo, Ill.); Domnanovich; James R. (Elk Grove Village, Ill.) Assignee: Mosaic Imaging Technology, Inc. (Schaumburg, Ill.), U.S. Pat. No. 6,242,743, Jun. 5, 2001). The system described in this patent comprises a plurality of detector modules positioned close to the object and equipped with high-resolution collimators in a combination of application-specific acquisition geometries and non-orbital detector module motion sequences composed of tilting, swiveling and translating motions, and combinations of such motions. Various kinds of module geometry and module or collimator motion sequences were considered. The considered applications include imaging human organs, such as head, breast, extremities (leg), etc, in addition to small animal imaging. However, the main focus of that technical approach is on a stationary aspect of the system that can be used as a bed-side compact imager in clinical applications. The tilting, swiveling and translating motions, are to collect more tomographic projections to assure higher quality imaging and it has merit in the clinical situations with sick bed-ridden patients etc, but this is a rather complicated and not well optimized approach for small animal imaging application.

Finally, among the potentially relevant prior art to mention are the software-based efforts of improving 3d reconstruction of the dynamic SPECT data based on a limited angular information obtained with standard slowly rotating/orbiting clinical SPECT systems. Standard reconstruction techniques do not allow temporal information to be obtained from this inconsistent projection data and may also create serious image artifacts which may lead to errors in diagnosis. Much better results are obtained using tomographic techniques such as PET or (as discussed above) ring camera SPECT where all projections of each image are acquired simultaneously. However, both PET and ring SPECT systems are more expensive and less common than SPECT systems which are available in almost any larger hospital.

The stated ultimate goal of the dynamic SPECT project (dSPECT) is to develop an imaging method suitable for functional dynamic studies which would use standard clinical equipment and standard data acquisition protocols and provide temporal in addition to 3-dimensional spatial information about the changes of activity distribution in the body. The dynamic SPECT (dSPECT) method can be used with all standard, currently available SPECT systems which means single, double and triple head cameras. The result of the dSPECT reconstruction, which includes attenuation and resolution recovery corrections, is a 4D data set, composed of a time-series of 3D SPECT images (3D movies). The dSPECT reconstruction is based on a mathematical optimization procedure where all the dynamic projections are considered simultaneously. It has been shown that dSPECT reconstructed dynamic images have better signal to noise ratios than those obtained by the "fast-rotation" method, where several data sets are reconstructed separately.

While showing some interesting possibilities, the above effort will most probably never be able replace the full data set obtained by the relatively rapidly rotating system described herein, and therefore is not considered an option for small animal imaging.

In a very recent paper Maddula et al (Dynamic Cardiac SPECT Imaging Using a Stationary SPECT Camera, R. Maddula, R. Clackdoyle, J. Roberts, E. Di Bella, Z. Fu, presented at the IEEE 2004 Medical Imaging Conference, Oct. 16-22 2004, Rome, Italy), describe a novel clinical cardiac SPECT camera (DyRoSH system) with the capability to collect full tomographic data every 2 seconds. The proposed camera uses three stationary detectors mounted with slant-hole collimators that rotate at about 30 rpm. Because the detectors are stationary, they can be placed much closer to the patient for improved spatial resolution. With Monte Carlo simulations and list-mode reconstructions, the authors compared the performance of conventional 3-headed SPECT with the proposed stationary SPECT system to estimate the kinetic parameters of two-compartmental model of myocardial perfusion. The study separated the effects of fast temporal scanning speed and better spatial resolution of DyRoSH scanner in estimating the kinetic parameters of myocardial perfusion accurately. The proposed system showed better accuracy in estimating kinetic parameters compared to conventional SPECT scanner. Again, the concept of rotating slant collimators limits the useful field of view and while it is well adapted to imaging of a human heart it cannot be easily scaled down and translated to high spatial resolution imaging of a whole small animal, such a rat, requiring about 20 cm FOV along the length of the animal.

In summary, the previously proposed fast dynamic SPECT designs for small animals were based on a fixed diameter concept, where the system opening was pre-defined and as large as to accommodate the largest animal to study. For example, the scintillator in the form of annulus offers full-angle coverage, high system efficiency and high imaging granularity but due to the above mentioned size compromises, the resulting spatial resolution is suboptimal for imaging an object such as a small mouse. The very interesting design with rotating (pinhole or other) collimators allows one to avoid mechanical complexity of our proposed system where the whole set of detector heads with collimators has to rotate and relatively fast around the animal, but again that system does not offer a flexibility to be optimized for a particular imaging geometry. Finally, the pinhole collimator based systems, both rotating and stationary, suffer from small active field of view, and/or poor sensitivity. None of the discussed in the literature designs proposed high sensitivity and high spatial resolution fast dynamic tomographic (SPECT) imaging of a whole animal such as a rat.

Accordingly, there remains a need for a fast dynamic SPECT designs that exhibit high sensitivity and high spatial resolution fast dynamic tomography for small animals. While the gantry apparatus described herein goes far in providing an SPECT apparatus that meets these needs there remains the problem of calibrating the multi-headed tomographic imager in a common spatial coordinate system to provide the high sensitivity and high spatial resolution fast dynamic tomography images desired as described above.

OBJECT OF THE INVENTION

Is therefore an object of the present invention to provide a method of calibrating a multi-headed imager in a common spatial coordinate system, i.e. determining the relative spatial position and orientation of the detectors with respect to each other and to the axis of rotation, to provide high sensitivity and high spatial resolution fast dynamic tomography images of the type described above. Such relative spatial information is critical for accurate localization of emission events in image reconstruction.

SUMMARY OF THE INVENTION

According to the present invention there is provided a method for calibrating multi-headed high sensitivity and high spatial resolution dynamic imaging systems, especially those useful in the acquisition of tomographic images of small animals. The method of the present invention comprises: simultaneously calibrating two or more detectors to the same coordinate system; and functionally correcting for unwanted detector movement due to "gantry" flexing. As used herein, the term "gantry" is meant to define any structure that provides support and movement capability to a plurality of sensors relative to a subject under study, one embodiment of which is described hereinafter.

DETAILED DESCRIPTION

What follows, is a detailed description of one SPECT multi-headed imager system in which the calibration system described herein will find use. While the calibration system of the present invention is described primarily in connection with such a multi-headed SPECT imaging system that finds use in the study of small animals, it should be noted that the calibration system of the present invention will be useful in the calibration of any multi-headed imaging system, PET, X-ray, etc. that rotates about a subject under study and utilizes imaging heads that are "gantry" mounted.

A knowledge of the dynamic biodistribution on a short time scale of minutes or even seconds of an injected or otherwise animal body administered imaging biomarker used either in diagnostics or in treatment, is crucial in many biological studies requiring measurement of blood flow distribution after biomarker injection, and subsequent uptake and washout by all organs, for example, in studies of the toxicity of novel imaging agents and pharmaceuticals such as those based on nanoparticles.

Standard SPECT scanners and scanning procedures, used both in human and small animal systems, generally do not allow for 3d imaging of the bio-distribution of the injected compound within such short (on the order of seconds) time increments. To the contrary, typically the SPECT images are summed averages over the total scan time and do not produce time snapshots of the distribution. Thus, they cannot be used to define dynamic bio-distribution (or pharmacodynamics).

Thus, the motivation behind the development of small animal SPECT imaging systems is to provide high resolution, high efficiency, and dynamic (with short time increments) imaging of the biodistribution of radioactively labeled substances (biomarkers) injected in the animal, from the moment of injection to the time end point of choice (typically continuous scans do not last longer than several hours to avoid animal exhaustion and/or the toxic effects of extended administration of anesthesia).

Figure 1:
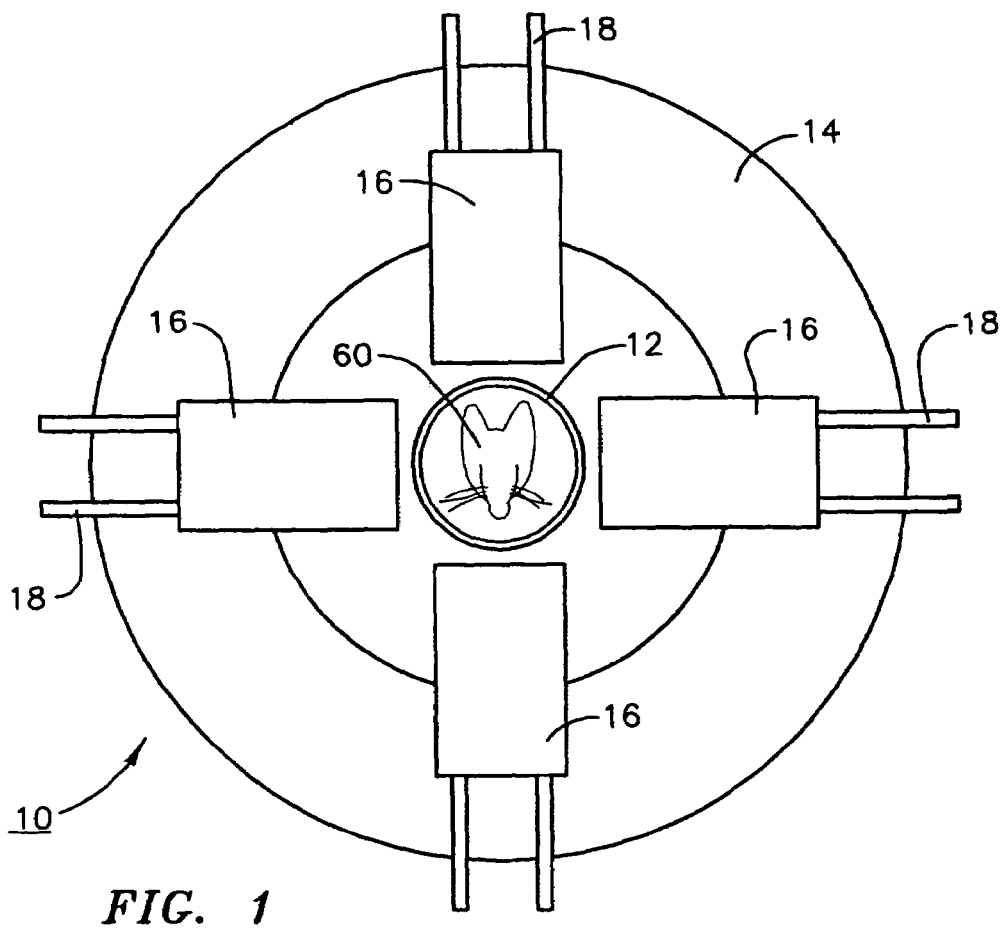
FIG. 1 is a schematic end view of the tomography system for small animals of the present invention.
Figure 2:
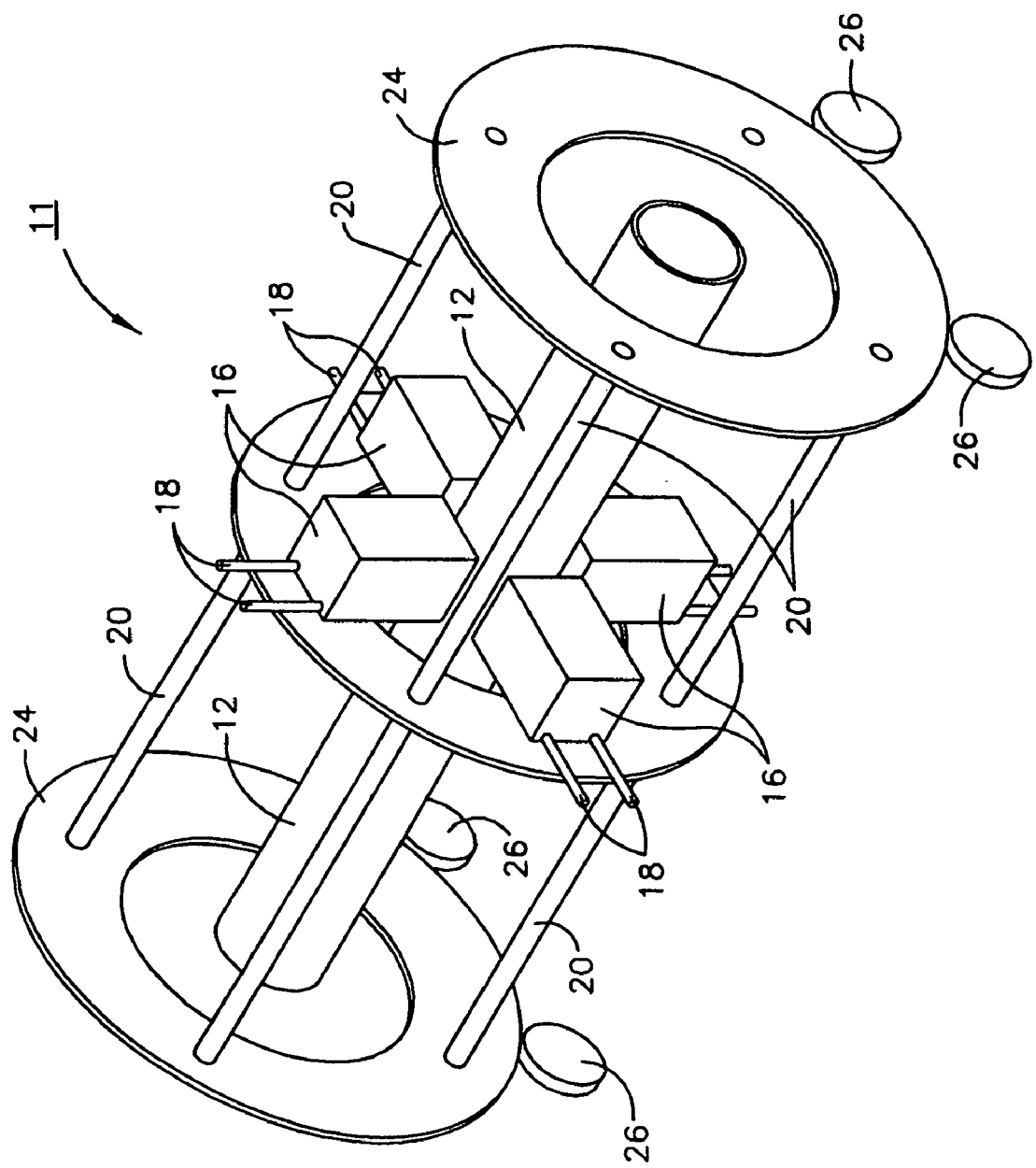
FIG. 2 is a schematic isometric view of the gantry of the tomography system for small animals of the present invention.

Referring now to FIGS. 1 and 2, a multi-headed imaging system 10 in its simplest embodiment comprises an animal containment tube 12, a rotatable mounting disc 14 for mounting a plurality of imaging heads or detectors 16 and rails 18 to which imaging heads or detectors 16 are movably applied and which rails 18 are in turn mounted to mounting disc 14 thereby allowing radial movement of imaging heads or detectors 16 relative to animal containment tube 12. As shown in FIG. 2 that depicts the gantry or mounting portion 11 of system 10. Gantry 11 may further include a frame 20 connected to a pair of drive discs 22 that can cause rotation of mounting disc 14 by rotational engagement of the outer peripheries 24 of drive discs 22 with drive wheels 26 that are driven by computer controlled motors (not shown). By a continuous rotation of detector heads 16 attached to mounting disc 14 on rails 18 around an animal contained in animal containment tube 12 at a relatively high angular speed (from few to many seconds per full rotation), the animal (not shown in these views) is viewed in a short time frame from all the angular directions, and therefore a high quality 3d tomographic reconstruction can be made by observing biological processes on a time scale of seconds. With continuous rotation of drive discs 22, frame 20 and ultimately mounting disc 14 with its attached detectors 16, a full 360 degree angular view can be subdivided into an almost infinite number of angular views/projections, allowing for high quality SPECT reconstructions. As will be apparent to the skilled artisan, in these and all other embodiments presented herein, animal containment tube 12 is fixedly/non-rotatably mounted at the center of gantry 11, i.e. in operation, tube 12 does not rotate with gantry 11 but allows for a contained animal (as shown below) to remain stationary as gantry 11 rotates about tube 12.

Figure 3:
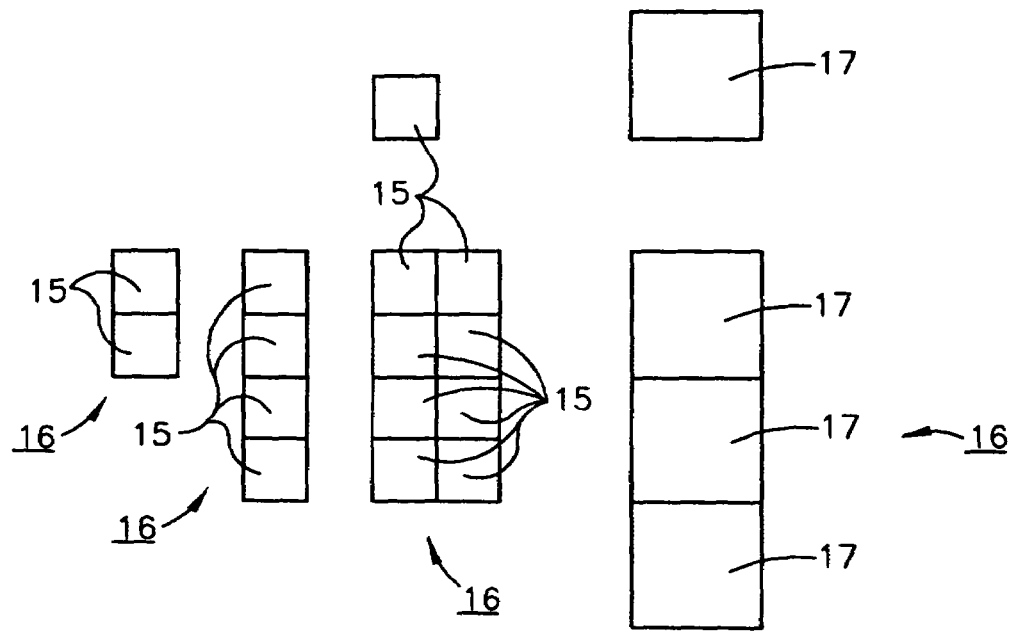
FIG. 3 is a schematic depiction of detector module configurations for forming different detector heads.

In FIG. 3, two basic sizes of the imaging photodetector modules or detectors 16 are shown forming different sizes of imaging heads 15 (~1 inch) and 17 (~2 inch). The active detector surfaces are shown as if looking form inside of the animal containment tube 12. To cover the animal over its entire length, each imaging head 15 or 16 comprises a set of usually more than one module 16. While smaller modules 15 can form detector heads 16 used to image animal sizes from small mice to large rats, it is more convenient to use fewer larger modules 17 for the same purpose, but this solution may be more expensive. The choice of module size and type may also be impacted by other considerations than mechanical properties and cost, such as imager performance.

Figure 4:
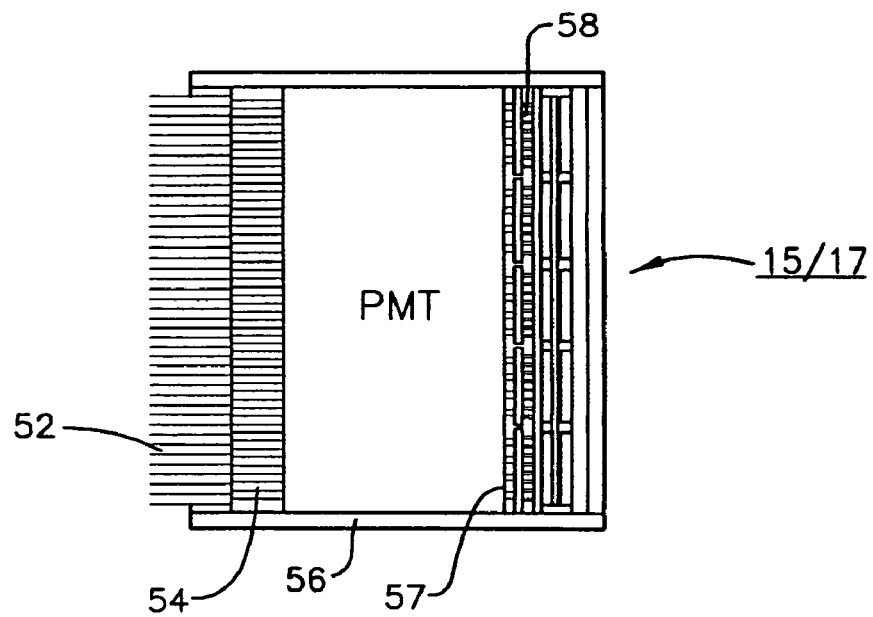
FIG. 4 is a schematic depiction of a single small-size detection module based on a single ~1" square PSPMT.

Referring now to FIG. 4 that is a schematic diagram of a small size detection module 15 based on a single ~1" square PSPMT (position sensitive photomultiplier tube) 50 comprising a parallel hole collimator 52, a scintillator with light guide 54, a tungsten shield 56 and electronic circuitry 58 of a type well known in the art, this single module can be use either as a mini-gamma camera with an active field of view of about 2.5 $cm^2$, or can be arranged as a bank of several of these modules 15 to make longer detectors 16 to cover the length of an animal such as a mouse located in the animal containment tube 12 as shown in the various examples that follow.

Figure 5:
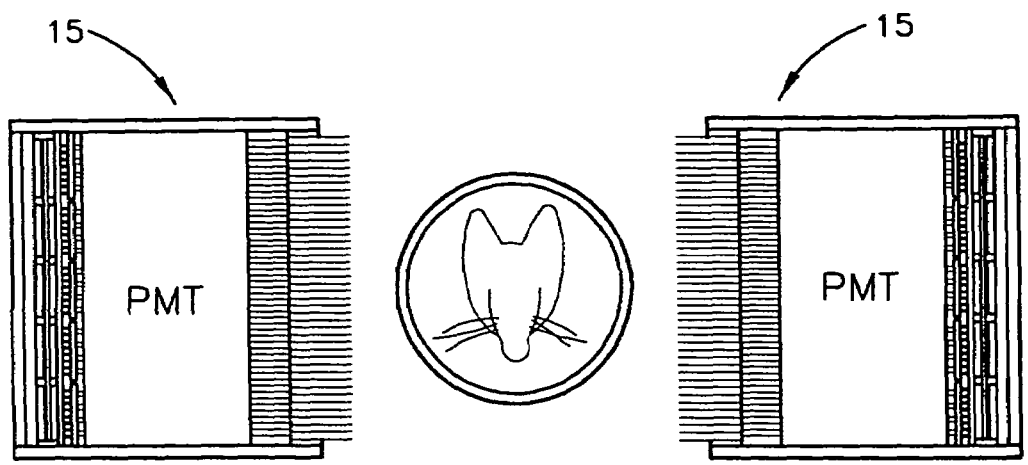
FIG. 5 is a schematic depiction of a module pair comprising two co-registered and aligned at 180 degrees detectors of the type depicted in FIG. 4.

Shown in FIG. 5 is schematic of a module pair made up of two co-registered and aligned at 180 degrees detectors 15 from FIG. 4 about an animal 60 contained in animal containment tube 12. This simple but quite powerful system is shown with mouse 60 placed inside of animal containment tube 12 of about 25-30 mm in diameter. Tube 12 allows for delivery of air and anesthesia to animal 60, as well as serving to maintain proper animal temperature during long scans.

Figure 6:
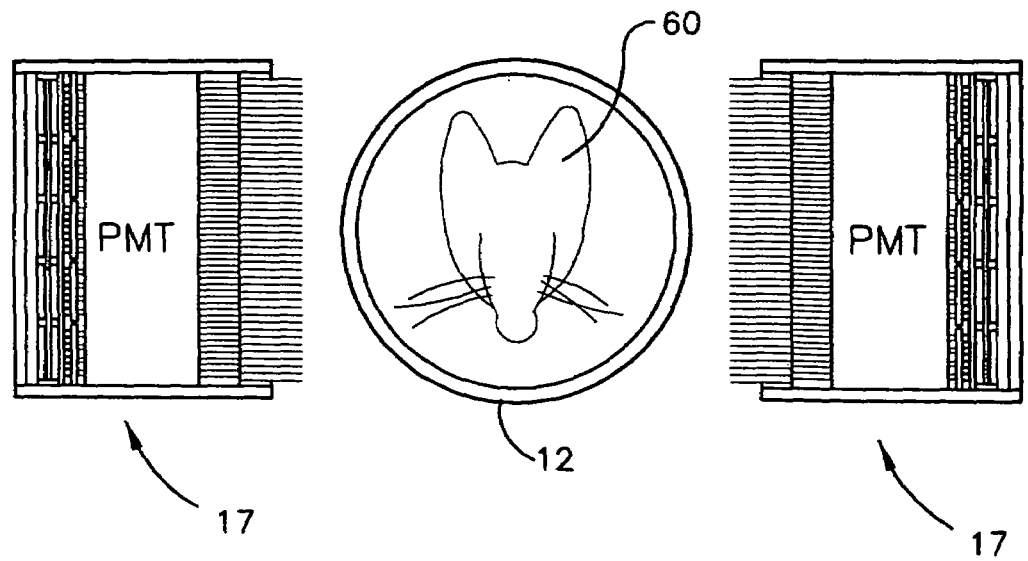
FIG. 6 is a schematic depiction of larger ~2" square flat panel PSPMTs used to image a larger animal, a rat.

Depicted in FIG. 6 is schematic of a system as shown in FIG. 5 except that a pair of larger (~2 inch) flat panel PSPMTs are used to image a rat-sized object 60. The linear dimension of the active field of view (FOV) of each of imager heads 17 is about double the size of those shown in FIG. 5.

Figure 7:
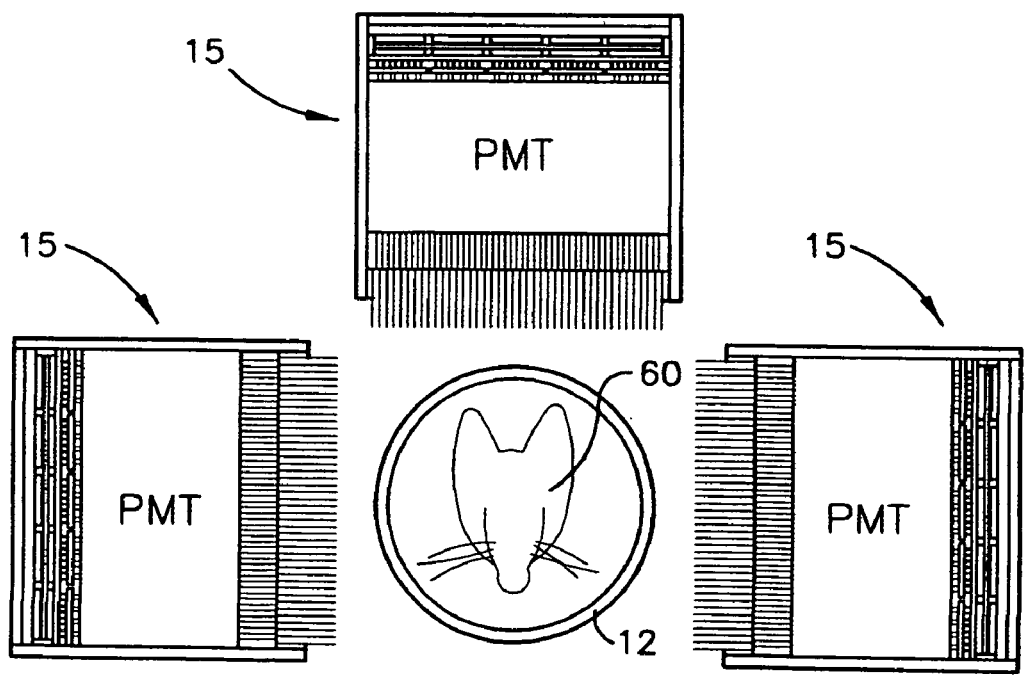
FIG. 7 is a schematic depiction of a high sensitivity arrangement with the closest placement of four detectors of smaller PMT modules (~2.5 cm square) with optimized angular coverage.
Figure 7:
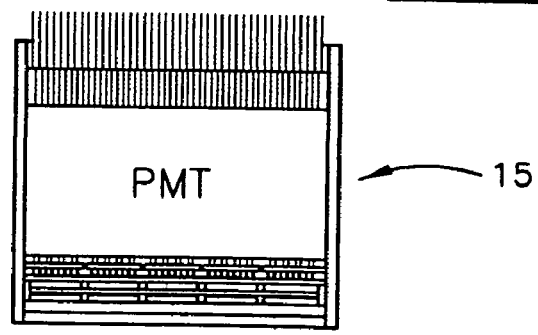

FIG. 7 depicts a high sensitivity imaging arrangement with the closest possible placement of four detector modules 15 made from the smaller PMT (photomultiplier tube) module (~2.5 cm) shown above and with optimized-angular coverage. In this case, two co-registered pairs of imaging detector modules 15 surround animal 60 in containment tube 12. The length of the modules (into the Figure) is four modules long (~10 cm). The assembly rotates around the animal with an angular speed defined by the time required for resolution of the dynamic study.

Figure 8:
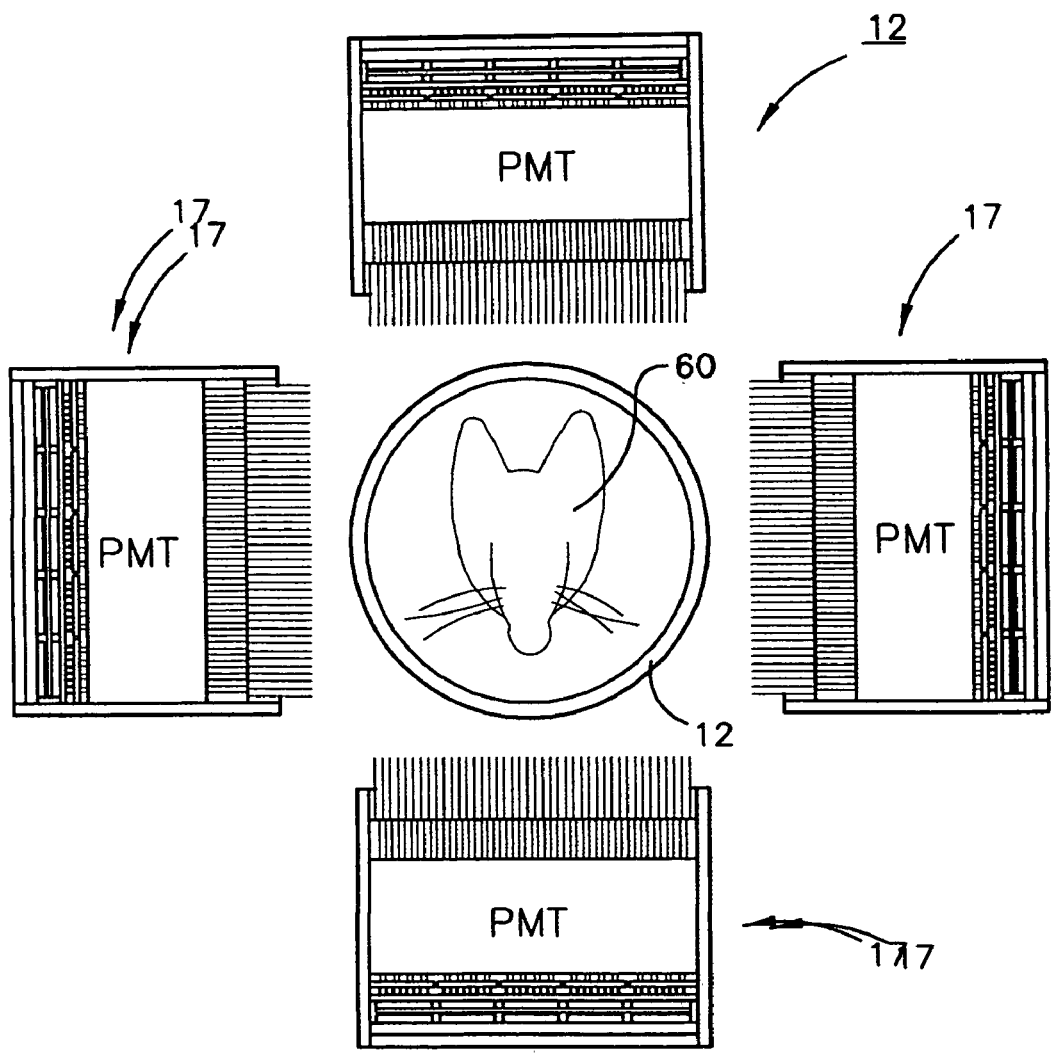
FIG. 8 is a schematic depiction of a high sensitivity arrangement with the closest placement of four larger detectors of flat PSPMT modules (~5 cm square) with optimized angular coverage.

FIG. 8 shows a high sensitivity imaging arrangement with the closest placement of four detector modules 17 comprising four flat PSPMT modules 50 (5 cm square) and with optimized angular coverage. Two co-registered pairs of imaging detector modules 17 surround animal 60 in animal containment tube 12. The length of the modules) into the Figure) is four modules in length or about 20 cm.

Figure 9:
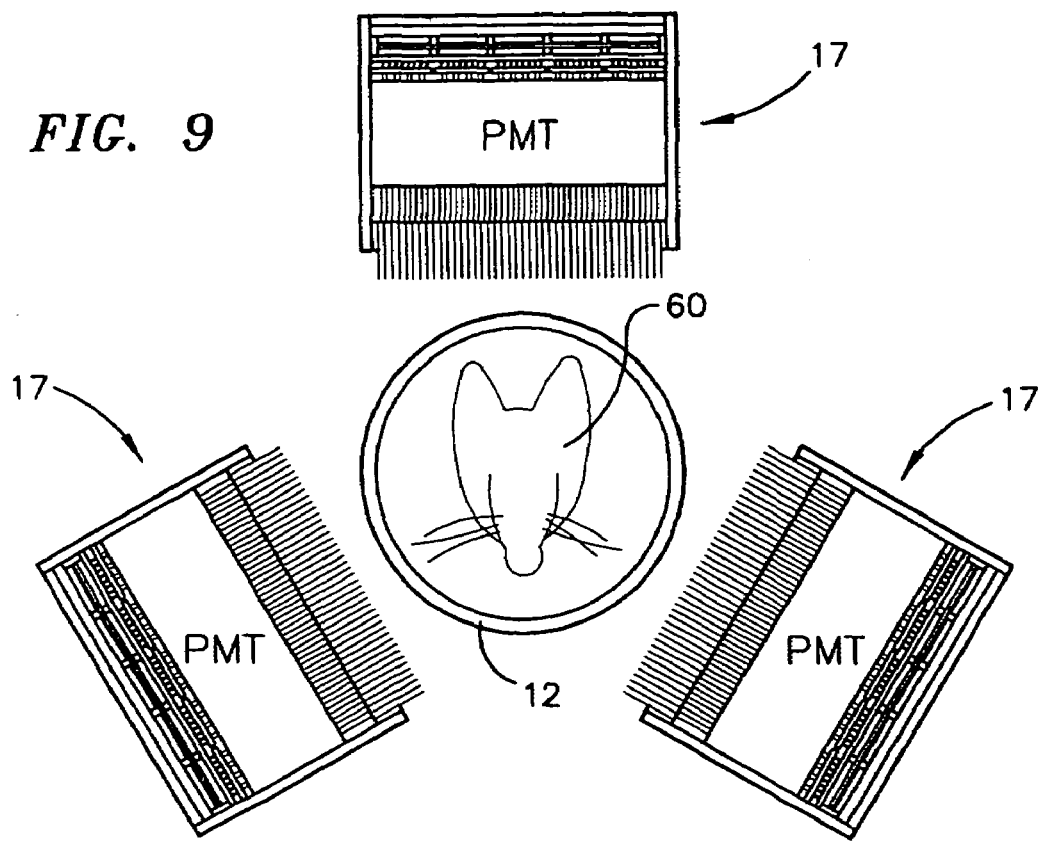
FIG. 9 is another example of a possible detector configuration.

FIG. 9 depicts another example of a possible configuration of detector modules around animal 60. In this example, three larger detector modules 17 are rotated about animal 60 in tube 12.

Figure 10:
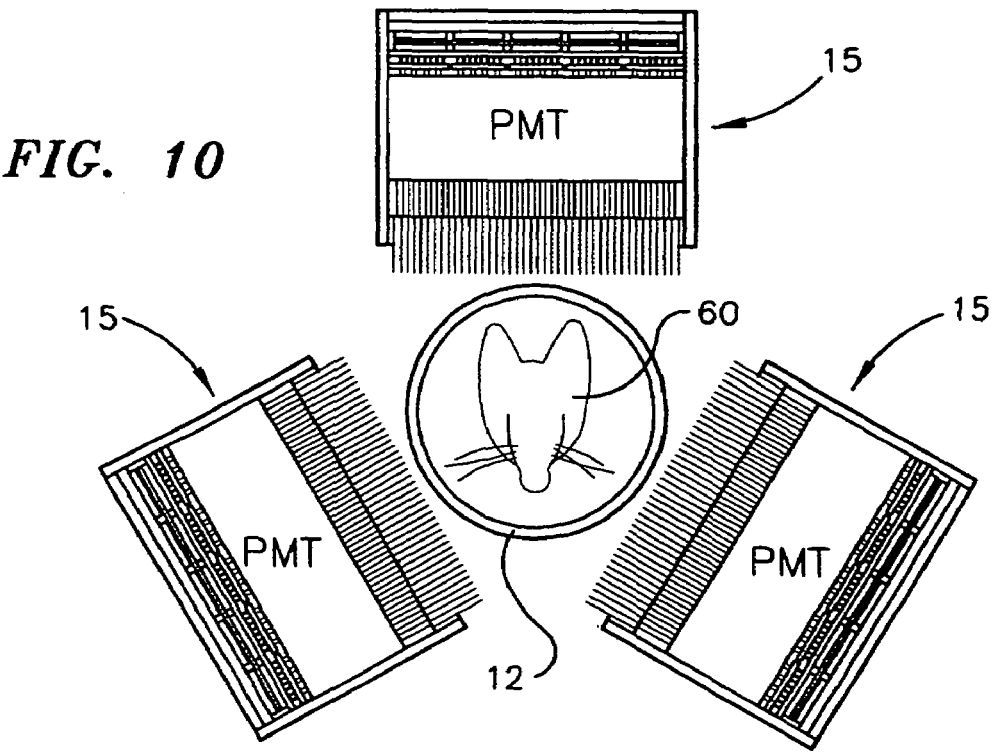
FIG. 10 is a schematic of the arrangement of FIG. 9 shown imaging a mouse.

FIG. 10 depicts the arrangement of FIG. 9 except with three smaller detector modules 17 about animal 60.

Figure 11:
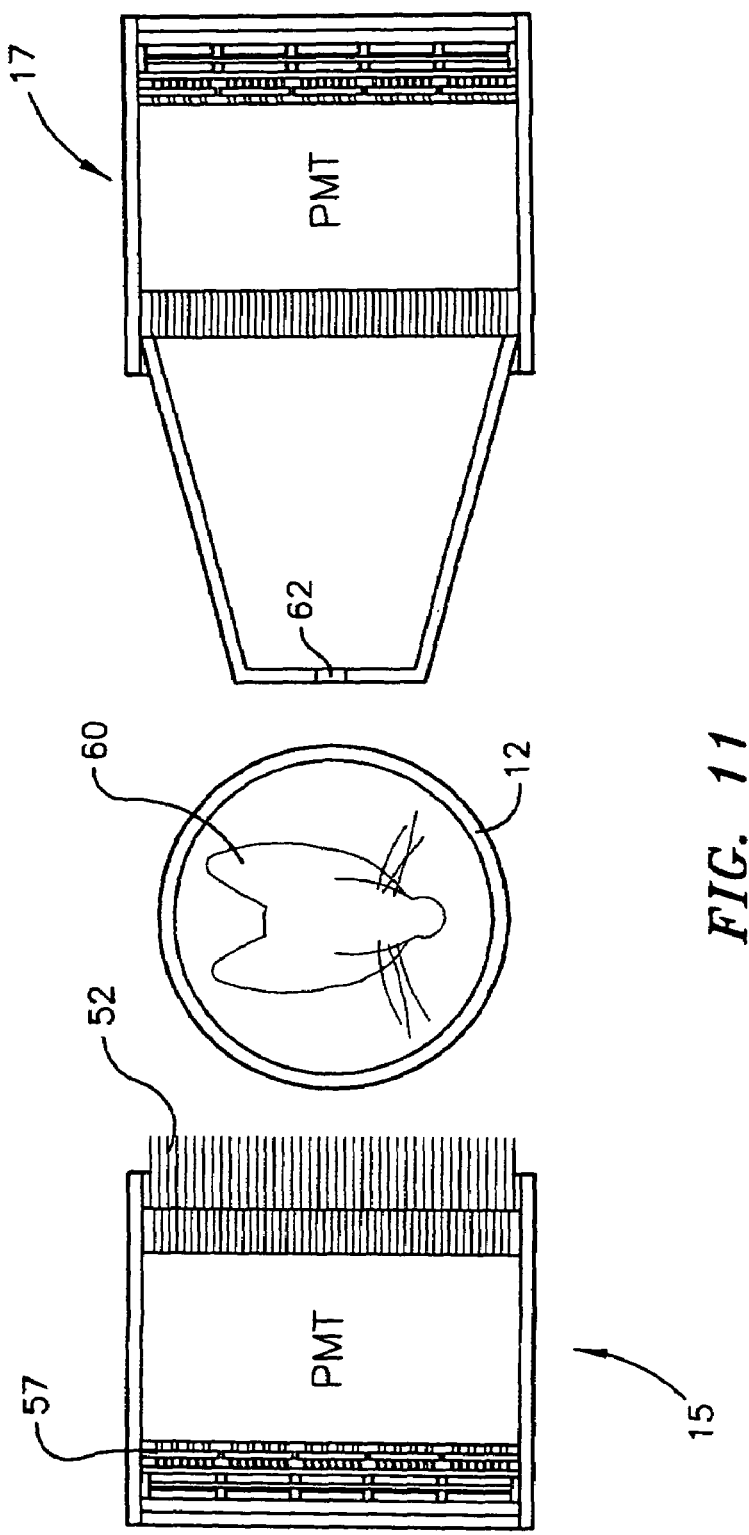
FIG. 11 is a schematic representation of a high sensitivity arrangement using a pair of opposed detectors one of which is a pinhole collimated detector.

Shown in FIG. 11 is one of many possible asymmetric configurations with a smaller vertical profile detector module 15 with a parallel hole collimator 52 at the left and a pinhole-equipped larger module 17 at the right. As will be obvious to the skilled artisan, this entire arrangement rotates about animal 60 as previously described.

Figure 12:
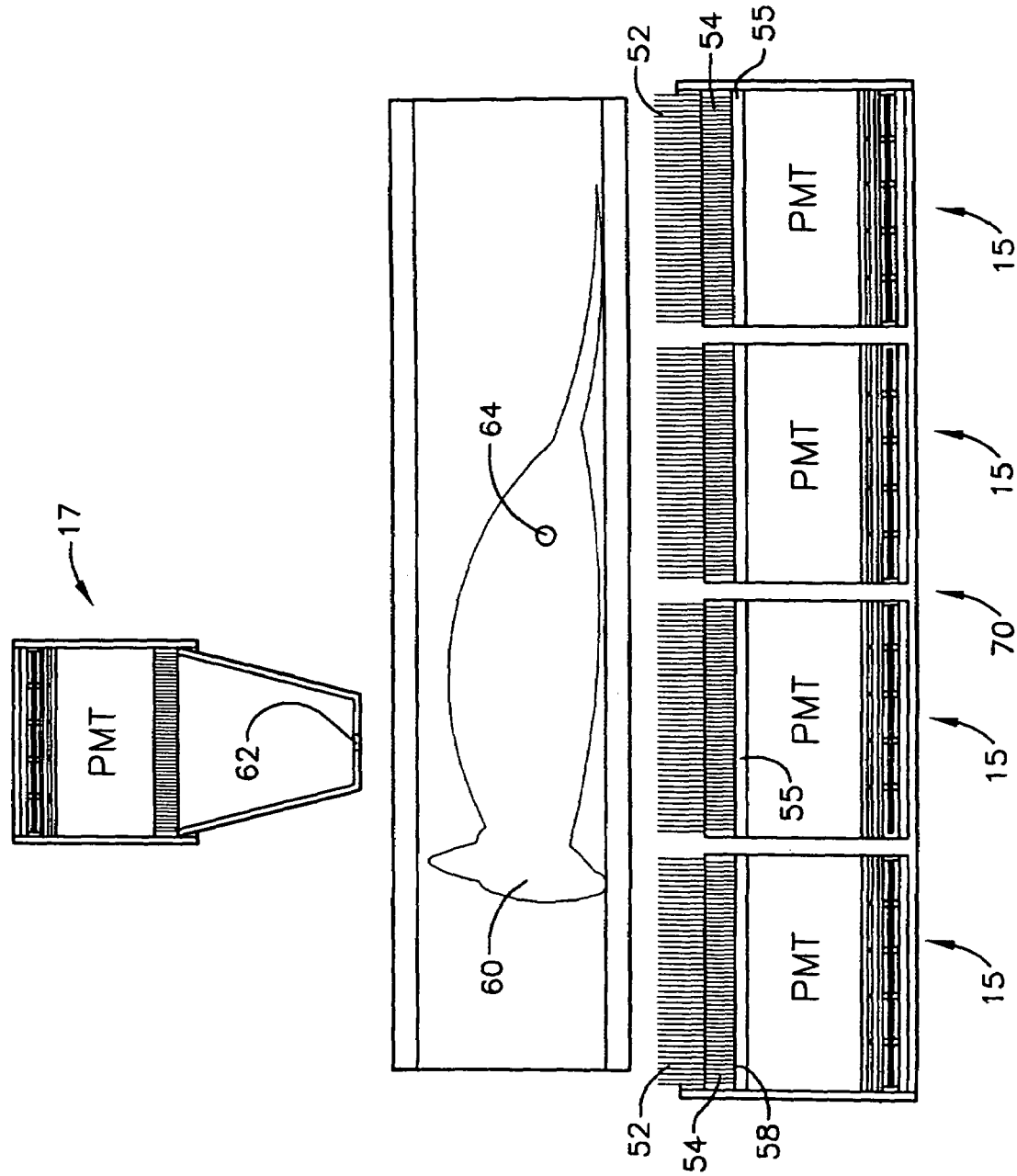
FIG. 12 top plan view of the system of FIG. 11.

FIG. 12 represents a top plan view of the system shown in FIG. 11. As shown in this Figure, the long detector 70 comprises four smaller PSPMTS 15 and covers practically the whole length of an animal 60, while the larger single pinhole based detector module based on a larger flat PSPMT 17 is focusing on imaging a single small region or organ of interest 64, such as the brain. Both detectors rotate about animal 60. More detectors can be placed around animal 60, as applicable and feasible, to provide more efficient coverage. The set of all detectors in this instance is mounted on the rotating structure as previously described. The properly sized scintillation arrays 54 are coupled to the selected photodetector modules 15. A very important issue is that the formed larger photodetector surface (from several individual modules 15) has no dead space in its response. This is assured by properly design of optical light guide couplers 55 inserted between scintillator arrays 54 and the photodetector array 57. Scintillation light originating from scintillation pixels placed above the junction regions between neighboring photodetectors is redirected away from dead edge regions to active regions of these neighboring photodetectors. Not all scintillation light collected from these pixels (the process is only partially efficient) but enough scintillation is detected to assure full detection efficiency and uniform response across all the FOV and the array of modules.

Use of the foregoing system and the approach described herein allows important dynamic behavior such as biodistribution changes of uptake and washout of a studied single gamma radio-labeled biomarker in each element of the animal body (within the field-of-view of the instrument) to be displayed and studied with high resolution tomographic 3d SPECT reconstruction on a short time scale of seconds.

Some of the key features of such a dynamic small animal SPECT design of the present invention are:

Dynamic tomographic measurements by relatively fast rotating gamma imaging detectors (~from 5-10 sec up/360 deg);

Large and flexible field-of-view (FOV) covering whole animal size;

Very flexible choices of imaging configurations due to modular detector structure;

Tight geometry of the detector modules surrounding the animal to achieve high spatial resolution;

Flexible imaging geometry optimization depending on animal size by using different sizes of animal-containing tubes and moving detectors 16 radially with respect to containment tube 12;

Use of parallel-hole collimators which assure high system sensitivity at a high spatial resolution level (as described in detail below);

T option of pairing imaging detectors placed at 1800 to each other, and on the opposite sides of the animal to permit use of combined (pixel-by-pixel) images in the image reconstruction. This special feature allows for substantially increased uniformity of sensitivity and spatial resolution in the whole animal, especially for radioactive labels emitting lower energy gamma rays, such as I-125 (27.35 keV).

All of which will be discussed in some detail below.

Additionally, system 10 may include additional features, depending on the system cost cap or other special desired properties:

Typically the system will permit imaging of the whole animal during the imaging session, however a simpler system versions will allow for only a fraction of the animal length to be imaged in one dynamic scan, for example head, or half of the body, etc.; and The parallel hole collimators on some or all of the imaging heads (as described below) can be replaced by pinhole collimators, allowing higher spatial resolution at the expense of lowered sensitivity, for example in imaging detail in the brain A very important flexible feature of the previously described imaging system is that it is possible to position detector heads 16 as close as possible to an animal (in containment tube 12) for a variety of animal sizes from small mice to large rats. This capability is necessary to achieve optimal spatial resolution and efficiency of the system for different animal sizes. This can be achieved by using several sizes (typically 3-5 types) of animal-containment tubes 12 and flexible positioning of the optimal number of detector heads 16 (typically 3-6) in a close geometry around tube 12. The system adjustment optimization procedure first involves animal sizing with proper tube selection, selection of an appropriate set of collimators (a combination of parallel hole and pinhole collimators) and then following with positioning of a selected number of detector heads 16 in positions corresponding to the tube size and depending on any other special requirements, such as the use of pinhole collimators to image only a selected organ. In the basic economical approach, the same number of detector heads 16 (typically 3-4) can be used for all animal and tube sizes.

The key technical components the fast dynamic small animal SPECT of the just described are:

detector heads are constructed of banks or arrays of individual compact gamma imaging modules typically arranged in rows along the animal body;

rotating cylinder, frame or similar structure with set of mounting fixtures on disks, rings, bars, etc providing mechanical support for the detector heads;

on-board data processing electronics (potentially including a data acquisition system and processors) mounted on the rotating part of the system (disk etc), separate from the electronics placed in detector heads 16;

animal containment tubes or containers (a set of different sizes) with a support mount;

Stationary support structure for the rotating part of the structure, including wheels, gears, motors, legs, table etc.;

Electrical cabinet/gantry with power supplies, UPS, signal processing electronics, data acquisition system and main on-board computer, as necessary; and Animal support systems, including anesthesia, temperature control, EKG, breathing, and other vital signals monitoring systems as required.

Two basic modes of rotation of the SPECT gantry with the set of imaging detectors mounted on it are envisioned:

Continuous rotation at an angular speed sufficient to rotate the gantry by an angle separating two neighboring modules in a time interval that is small as compared to the minimum required dynamic time bin for the studied dynamic phenomena.

Pendulum-type rotation with the gantry rotating by an angle equal to the angular separation between the neighboring imagers and then changing the direction of rotation to go back to the starting position. Time period (time for one-way swing) for this rotation mode should be small when compared to the required minimum time bin of the dynamic plots, as above. The detectors will scan the object continuously on both directions of rotation.

In both modes of rotation, the optimal time period will be defined based on particular requirements of the study being performed and the requirements of the implemented tomographic reconstruction algorithm. In both cases a time and angle stamp will be put on each recorded gamma event for later dynamic tomographic reconstruction.

As an example, a requirement of a tomographic reconstruction with a 10 sec dynamic time bin of a whole animal, or only of a studied organ, could be potentially accommodated by a 3 sec one-way pendulum time period (6 sec full pendulum swing). The low limit in the time period will be dictated by the mechanical issues such as friction and accelerating and decelerating forces at the reverse rotation points. This difficulty is to be balanced against the complications related to continuous rotational mode when all the electrical contacts need to be either wireless and/or of a slip-ring type rotary interface. Which of the above modes of rotation will be preferred will depend on the actual mechanical and electrical parameters of the planned actual structures. In principle, the continuous rotation mode offers the best performance with a uniform rotation speed and it is therefore the preferred mode of rotation. As an example, in a two-opposed pair imager system (four detector heads placed at 90 deg), and assuming a 10 sec time bin, the required uniform rotation speed of the gantry is estimated at about 30° per second, which for small rotating systems intended for small animal imaging is entirely feasible.

A potentially intermediate solution permitting the avoidance of the complications of a continuous rotation and at the same time minimizing the effects of direction reversal in the pendulum mode is to apply a larger rotation angle, say 360° before reversing direction of rotation. In the above example, the full rotation period by 360° will take about 12 seconds.

Data transfer from rotating heads 16 can be achieved in several ways. In the first and preferred mode of operation, each detector head 16 can act as a separate entity with data collected, pre-processed and digitized in an on-board processor and then sent in the digital form to the next level computer/processor for further data analysis, processing and image reconstruction.

Data transfer from rotating heads 16 can be achieved by an optical, wireless, or rotating contacts (slip-ring) method, or a combination of these techniques. The main advantage of the individual head method is the highest achieved flexibility of the setup allowing easy implementation of different configurations of the system, as discussed above. In addition to proper mechanical mounting fixtures and alignment tools, each detector head 16 may be equipped with 3d positioning sensors, allowing for direct control of its position relative to animal containment tube 12 and an animal in tube 12. Digital position data and time stamp data will be added to each recorded event in every detector head.

In a second major option, the information/data (in analog or digital form) from all detector heads 16 mounted on rotating ring/plate 14 is first transferred and digitized in a common processor, placed on the rotating disc/ring of the gantry. After processing, the data is then transferred to the outside processor via a proper digital data connection including slip-ring and/or wireless/optical links.

In the fully analog version of the data transfer system, all the analog signals from the sensors and placed in detector heads 16 are transferred via a proper slip-ring rotating electrical connection and all the signal digitization is performed outside the rotating part of the gantry. While potentially least complicated, this solution can easily suffer from the signal/noise issues and is considered the least preferred.

Finally, the pendulum type rotation mode discussed above, will in principle require a standard cable connection, with the only added condition of a flexible cable link allowing for limited angular movement of the rotating detector assembly.

Other methods for data transfer can be envisaged as variants or combinations of the above outlined basic scenarios.

Additional data transferred from detector heads 16 and other rotating parts of the gantry (mounting disc 14, etc), to the stationary components of the system (computer 40, etc) can include temperature, humidity, magnetic field values, low voltage and high voltage values, and other electronic and environmental parameters that may be monitored to assure proper operation and calibration of the system. Digital signal or analog signal inquiries or requests generated by the control software on any computer/processor used in the system can be sent via the analog and data link back to the stationary and rotating components to perform remote check system operation and calibration. An example of such a control signal transfer could be adjustment of the operational high voltage or amplifier gain on the detector head(s).

Gamma radiation sensors and electronics placed on the rotating heads or on any other rotating part of the system such as a common mounting disc 14, need low voltage and high voltage power for operation. While battery operation is possible with batteries mounted on heads 16 and/or on the disc 14, the preferred solution is to deliver all the necessary power via a slip-ring solution, using standard developed approaches.

The number of the detector heads 16 in the system will depend on the implemented configuration and can be odd (1, 3, 5, etc) or even (2, 4, 6, etc). Typically the detector heads will be distributed symmetrically on a ring at equal azimuthal angular steps around an animal placed in tube 12, but in some situations other asymmetrical configurations may be selected. In the case of even number of detector heads, the heads placed at 180° to each other can be naturally paired to offer the special adjunct imaging mode when two aligned detectors on both sides of the animal can be used to produce combined images, in addition to the standard individual data reconstruction mode. This mode of operation requires more precise mechanical alignment of the opposed detector heads 16 in a pair, and special treatment (a form of multiplication) of imaging data performed in the reconstruction software. Except the mechanical alignment condition, there are no other additional requirements to operate the system in this mode. Data can be reconstructed in the standard mode with all data treated individually from all detector heads 16, or in the combined pair mode with data first combined from two detector heads 16 in each opposed detector pair prior to reconstruction. This mode of operation is known to provide a good measure of automatic gamma ray absorption correction and improves spatial resolution and contrast in the reconstructed images. Typically in this mode, two opposed detector heads will be equipped with identical parallel-hole collimators. Other pairs can have other, but still identical, collimators selected.

In the case of odd number of detector heads 16, limited pairing can also be realized. For example for 3 detector heads, 2 can be placed in an opposite pair, while the third can be used as an individual imaging head and can be for example equipped with a different type of a collimator, such as a pinhole. In this situation there are many variants of the detector head placements and generally these configurations will not be symmetrical. It is also possible that the system be composed of several different detector head types, optimized for different imaging situations for different animal sizes, required spatial resolutions and sensitivities. In a standard system, all detector heads 16 will be identical, but can be equipped with different collimators.

As design of the rotating scanner concept allows for maximum arrangement flexibility, this design can also accommodate use of pinhole collimators on all or some of the imaging modules, in lieu of the standard parallel hole collimators. Typically, as is also practiced in clinical SPECT, at least three types of parallel hole collimators can be implemented, allowing for flexibility in collimator selection depending on the imaging project (radiation uptake, size of the region to image, length of time intervals, the animal size—mouse or rat, etc).

Detector heads 16 should provide efficient gamma detection with good intrinsic special resolution for a variety of gamma emitters, especially such as I-125, Tc-99m, In-111, and I-123, and have a compact design. Different detector technologies can be selected for this application, some based on scintillators and compact photomultipliers, and others on solid state type sensors such as zinc telluride, cadmium zinc telluride, mercuric iodide, and other. Also a combination of a scintillator gamma sensor and a solid state photodiode array may be used. The preferred design of the proposed system is based on a pixellated scintillator array coupled to a single or an array of position sensitive photomultipliers. Several materials can be considered for the scintillator: NaI(T), CsI(Na), CsI(Tl), GSO, YAP, LaCl3, BrCl3.

Containment tube 12 in which the animal is placed serves several purposes:

Provides stable bed-type support for the animal during scan.

When properly constructed and ventilated, it provides animal with necessary and comfortable conditions for a valid in-vivo scan.

Limits the transversal size of the scanned object by placing the animal extremities within the geometrical constraints of the tube, out of the way of the rotating heads and other rotating and stationary components of the system.

Secures that no connections, wires and cables to and from the sensor and probes placed next to, in, or on the animal, and anesthesia gas tubes, can extend into the path of the rotating components of the system.

Potentially provides animal container in which the animal can be carried to other imaging systems, such as MRI or CT, for additional imaging and later fusion of the images from the involved modalities for better visualization of the involved organs and fuller analysis of the dynamic phenomena under study.

Provides an animal containment volume in awake animal studies when no or only limited anesthesia is used. In such cases visual-light absorbing (for comfort) and infrared transmitting (for external animal monitoring) tube material will be selected.

From the above discussion, several sizes and types of tubes with different physical properties can be used with the system, depending on the kind of the biological dynamic study being performed, and the potential involvement of other imaging modalities.

Rotating structure 15 to which detector heads 16 are attached can be, for example, in the form of an open cylinder with two disks at both ends providing stability and support during rotation frame or similar structure with sets of mounting fixtures on disks, rings, bars, etc providing mechanical support for the detector heads as shown in FIG. 2.

Another option (not shown in the accompanying Figures) comprises one solid disk with detector head mounting fixtures extending out of the plane of the disk. However, this type of structure is usually more difficult to make stable and light-weight. Whatever the particular design, a cylinder type structure provides a solid mechanical support in a relatively light and open structure with easy manipulation around the scanned animal.

The set of fixtures such as rails 18 or mounting holes placed on mounting disc 14 used to attach detector heads 16, should permit flexible adjustment of the detector heads to accommodate different sizes of animal containment tubes 12 and different detector heads 16 such as collimators, including pinhole collimators.

The fast dynamic SPECT system described above can also include other add-on imaging modalities such as TV camera for monitoring condition, comfort, and position of the animal, thermal imaging cameras (in addition to the temperature probes) to assure that the animal is kept at a proper temperature during the scan, and optical (infrared or visible) 3d monitoring system for accurate measurement of animal position or pose to correct for the animal movement during scan, which happens even under full anesthesia. The latter monitoring function is especially desirable in some studies when an animal is physically restricted to the volume of tube 12 but not placed under anesthesia. This type of special study is considered for measurement of dynamic biodistribution in organs and for processes when the effects of anesthesia may strongly modify the distribution of the tested biomarker or compound, as is often the case with small animal brain studies.

Although not an essential part of the system of the present invention, a small animal CT or microCT, or MRI imager can be used in conjunction with the described fast dynamic SPECT to provide anatomic details (organ map) of the scanned animal to facilitate proper attribution of the detected and measured dynamic distribution of the radio-labeled compound. The animal can be moved between these modalities in the same detachable animal-containment tube 12 providing that the tube has proper magnetic (for MRI) and X-ray absorption (for CT) properties. While MRI system may have to be kept at least several feet away from the SPECT system due to adverse effects of the stray magnetic field on the active components of the SPECT system, the CT imager can be placed in a very close vicinity, adjunct to the SPECT scanner.

Thus, in summary, among the preferred features of the fast dynamic SPECT system described herein are:

Whole animals can be imaged with high sensitivity and from many directions at the same time, assuring fast dynamic imaging;

The compact gamma imaging heads rotate relatively fast (5-60 sec full 360 deg rotation) around the animal;

The animal is placed inside a cylindrical tube selected from several available standard sizes for optimized as-close-as-possible imaging geometry;

The detector heads with parallel-hole collimators are positioned as-close-as-possible to the tube surface (preferred option); when equipped with parallel collimators; but other positioning may be optimal for pinhole collimators In a preferred embodiment, data is digitized on board the individual rotating heads and is transferred from the rotating part of the system to the stationary part via a wireless/optical link.

Figure 17:
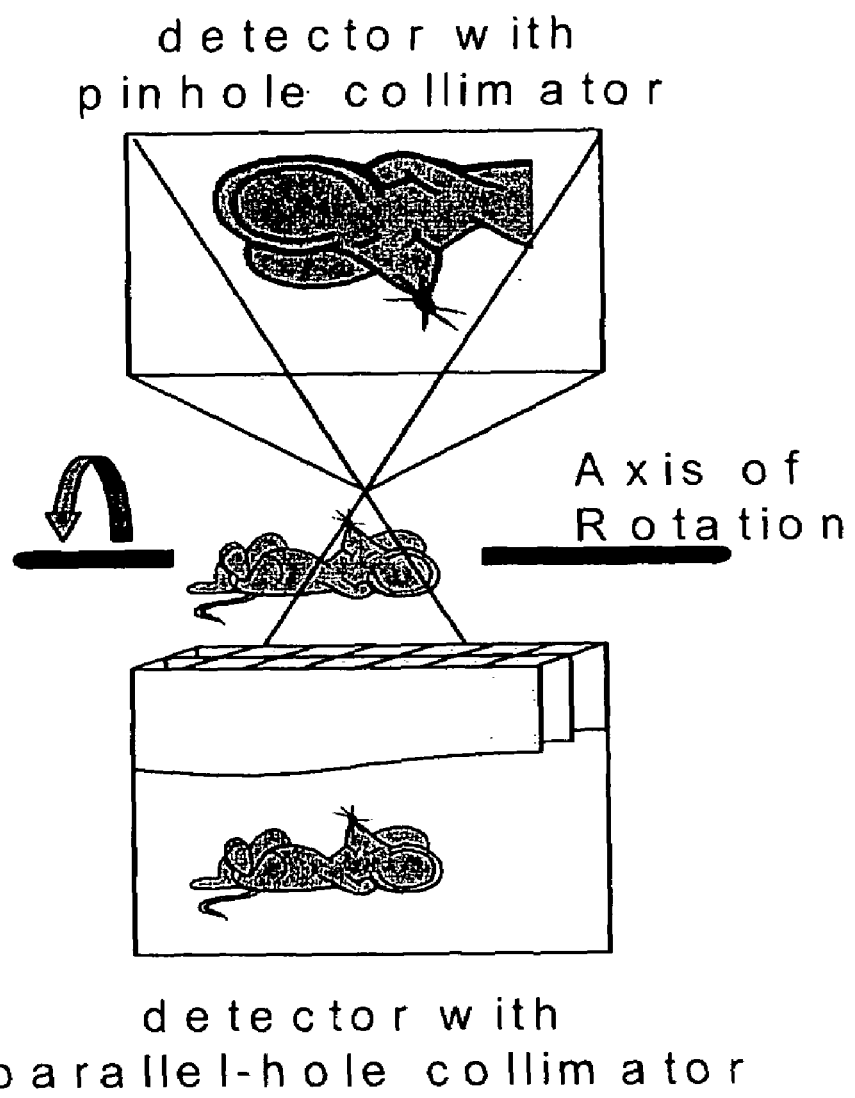
FIG. 17 is a schematic depiction of a test platform used in the evaluation of the calibration and correction method described herein.

For purposes of the following discussion, a SPECT imaging system having two gamma-ray detectors and an optical tracking system designed to image live mice (as described in detail in A. G. Weisenberger, et al. "Development and Testing of a restraint free small animal SPECT imaging system with infrared based motion tracking." NSS Conference Record, IEEE, 2003 and J. S. Goddard, et al. "Real-time landmark based unrestrained animal tracking system for motion-corrected PET/SPECT imaging." NSS Conference Record, 2002 IEEE, 2002, both of which papers are ncorporated herein by reference in their entireties) is modeled. (See FIG. 17 for a schematic depiction of such a system.) The gamma detectors have a 10×20 $cm^2$ field of view and are constructed using 2×2×15 $mm^2$ pixilated NaI (TI) scintillators. For a pinhole camera a model of projection geometry can be characterized by seven parameters, while for the detector with a parallel-hole collimator, the geometry can be characterized by five parameters. The parameter values for a particular geometry can be accurately determined by non-linear least squares iterative fitting. For geometry calculation, we used 360° of projection data of a calibration phantom composed of three point sources arranged in a triangular arrangement as described by D. Beque, et al. "Optimization of pinhole SPECT calibration", presented at Nuclear Science Symposium Conference Record, IEEE, 2003. In the work described below two additional parameters were introduced for each detector to model the observed axial excursion due to flexing of the detector gantry. In addition, a phase angle between the two detectors was also fitted. The projection data from both detectors can then be used to reconstruct the common object in the same space.

Figure 13:
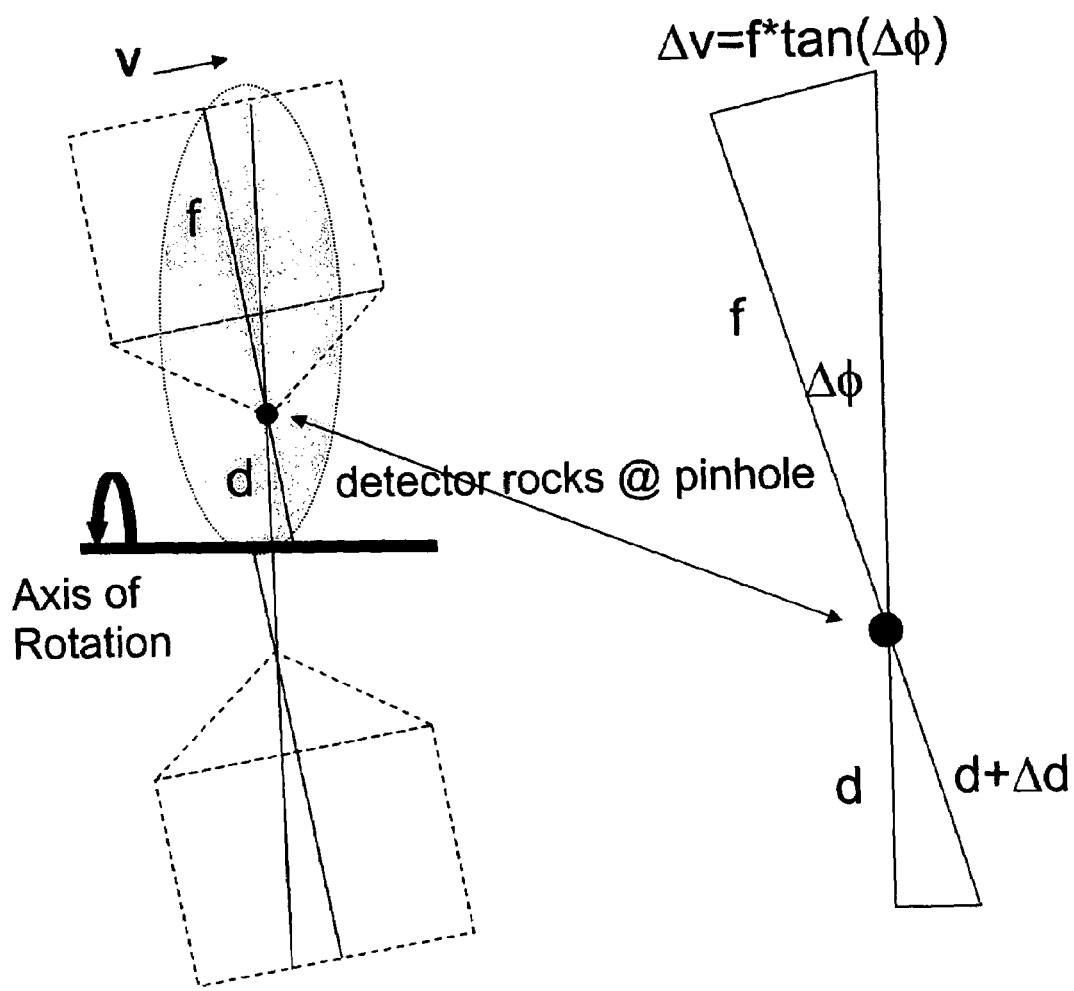
FIG. 13 is an illustration of projection shift, $f \tan(\theta)$, for a rocking detector.

As previously noted, while the imaging system described hereinabove and similar multi-headed imaging systems provide significant advantages as recited above, undesirable detector motion can arise from a combination of gantry flexing and possibly axial travel in the bearing support. This motion can cause a definite angle-dependent movement between the detector and the axis of rotation. The effect is observable by a predictable angle-dependent movement in the projection image. In the case of the device as just described, the movement is predominantly in the axial direction. Flexing and travel can occur in several ways depending upon the strength and location of detector support to the gantry. As a result, an appropriate correction function may be specific to a particular gantry design. FIG. 13 shows how an undesirable gantry motion manifests itself as a small rocking motion when the heavy detector is supported by a metal bracket on one side of the detector. At the top of the detector (0 degrees) gravity induces a turning moment, pulling the detector downwards slightly on the side where the turning moment is greater. In the case shown in FIG. 13, the turning point will be at the position of the bracket since it is the weakest part of the gantry support. After 180 degrees of rotation, the detector orientation is shown at the bottom of FIG. 13. In certain cases, the undesirable rocking motion may be approximately modeled as a small oscillation of the angle θ at a pivot point near the pinhole, in the plane containing the axis of rotation and the pivot point.

Figure 14:
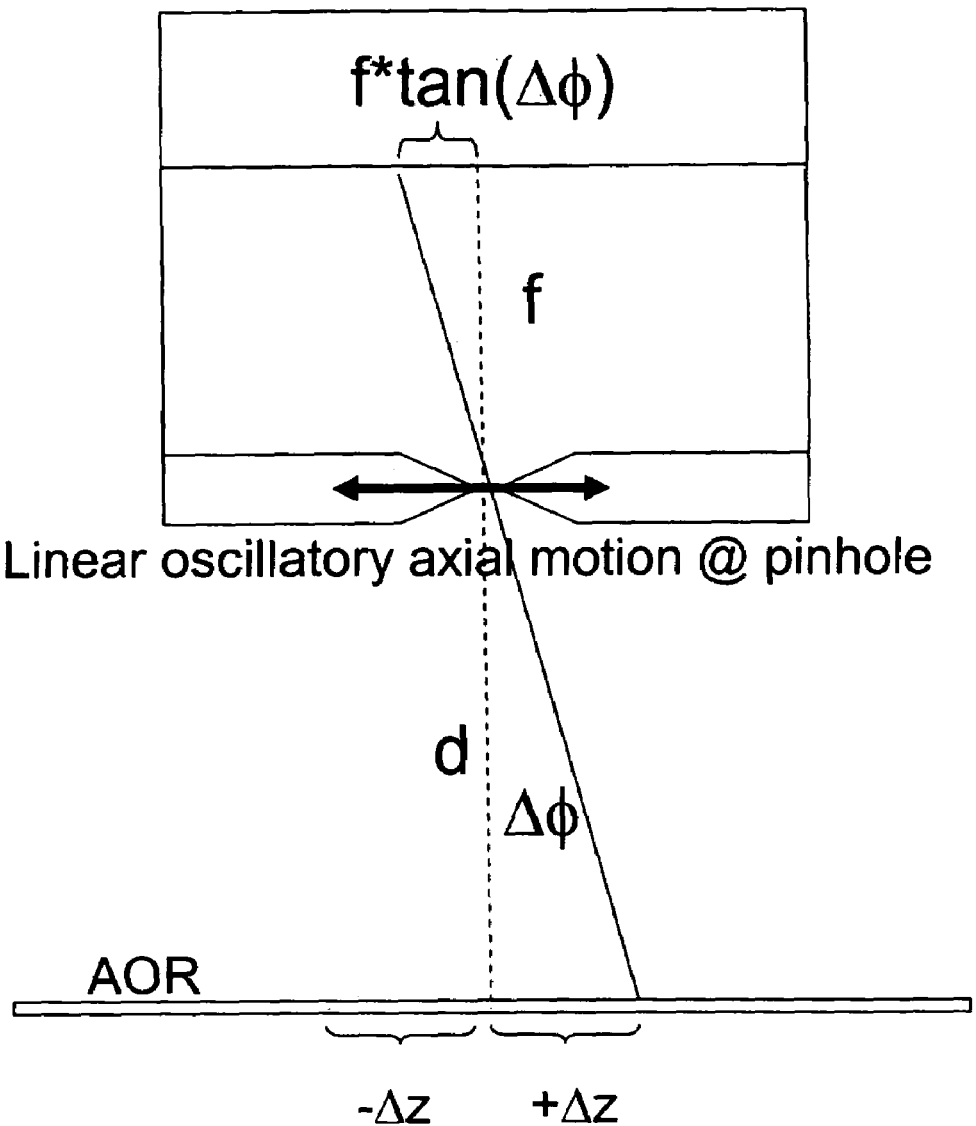
FIG. 14 exhibits the assumption of the corrective method of the present invention that an axial sinusoidal motion of amplitude z occurs at the pinhole of each detector.

Referring now to the accompanying FIGS. 13 and 14, The projection shift $\Delta v$ in a multi-headed system can be analyzed using the partial derivatives of the pinhole projection model, $v = fz/d$, where v is one of the two orthogonal coordinates (u,v) defined in the plane of the detector; and f and d are the focal length and distance from axis of rotation to the pinhole respectively. The postulated rocking of the whole detector at the location of the pinhole alters the parameter values for d and the origin of the z-axis. The projection shift $\Delta v$ can be approximately expressed as:

$$\Delta v = \frac{f}{d}\left(\Delta z - \frac{z}{d}\Delta d\right)$$

where $\Delta z = d \tan(\Delta \phi)$ $\Delta d = d(1/\cos(\Delta \phi) - 1)$

Here $\Delta z$ and $\Delta d$ are functions of the tan and cosine of the rocking angle $\Delta \phi$ respectively. At small tilt angles near zero, it is anticipated that $\Delta z$ has a greater effect on $\Delta v$ than $\Delta d$ does at the focal region where z/d is less than 1. Therefore, we propose a simple model for gantry motion correction, where the correction term is an oscillatory expression due to the $\Delta z$ component only.

$$\Delta v \approx \frac{f}{d}(d\tan(\Delta\phi)) = f\tan(\Delta\phi)$$

This approximate expression for $\Delta v$ is made clearer when one examines the depicted projection shift $f\tan(\Delta\phi)$ in FIG. 13 (enlarged portion). Over a complete revolution, the loci of the pinhole describes a circle in a plane that is inclined at a small angle ($\alpha\phi$) to the normal of a rotation axis. The amplitude $\Delta z$ of axial oscillatory motion is given by $d \tan(\Delta\phi)$. The parameter $\Delta z$ is an additional parameter that needs to be fitted. The instantaneous axial displacement g is given by $g = \Delta z \sin(\theta + \xi)$ where θ is a known detector rotation angle. Besides $\Delta z$, the initial detector angular position ξ is another parameter that requires fitting. Similar expressions can be derived for the case of parallel-hole collimators.

The axial motion term g is along the z direction. It is augmented to the z-coordinate before the 3-orthonormal correctional transformations, as described by Beque. The rotational transformations align the coordinate system of the source with that of the detector. The angles (θ, φ and ψ) are rotations about the z-, x- and y-axes, respectively.

$$\begin{bmatrix} x''' \\ y''' \\ z''' \end{bmatrix} = \begin{bmatrix} \cos\psi & 0 & -\sin\psi \\ 0 & 1 & 0 \\ \sin\psi & 0 & \cos\psi \end{bmatrix} \begin{bmatrix} 1 & 0 & 0 \\ 0 & \cos\phi & \sin\phi \\ 0 & -\sin\phi & \cos\phi \end{bmatrix} \begin{bmatrix} \cos\theta & 0 & 0 \\ -\sin\theta & \cos\theta & 0 \\ 0 & 0 & 1 \end{bmatrix} \begin{bmatrix} x \\ y \\ z+g \end{bmatrix}$$

After the 3-transformations, the resultant additional terms due to g are:

$g_{x'''} = -g\cos\phi\sin\psi$, $g_{y'''} = g\sin\phi$, $g_{z'''} = g\cos\phi\cos\psi$ Since φ and ψ are usually small angles, only the term $g_{z'''}$ has a real significance. The extension to Bequé's geometry calibration model is more apparent when projection equations contain the extra axial motion correction terms, $g_{x'''}$, $g_{y'''}$, $g_{z'''}$.

$$v = \frac{-f(m_v - z_0''' - g_{z'''})}{d - y_0''' - g_{y'''}} + m_v + e_v$$

$$u = \frac{-f(m_u - x_0''' - g_{x'''})}{d - y_0''' - g_{y'''}} + m_u + e_u$$

where u and v are coordinates in projection space (i.e. the detector coordinates); m and e are mechanical and electronic shifts. The triple-primed coordinates ($x_0'''$, $y_0'''$, $z_0'''$) denote the transformations without the axial motion term g, as first described in the cited Beque reference. It is clear that $x''' = x_0''' + g_{x'''}$ $y''' = y_0''' + g_{y'''}$ $z''' = z_0''' + g_{z'''}$ In this expression, the triple primed coordinates with the subscript "0" denote the transformation without the axial motion term g, as described in Beque.

Figure 15:
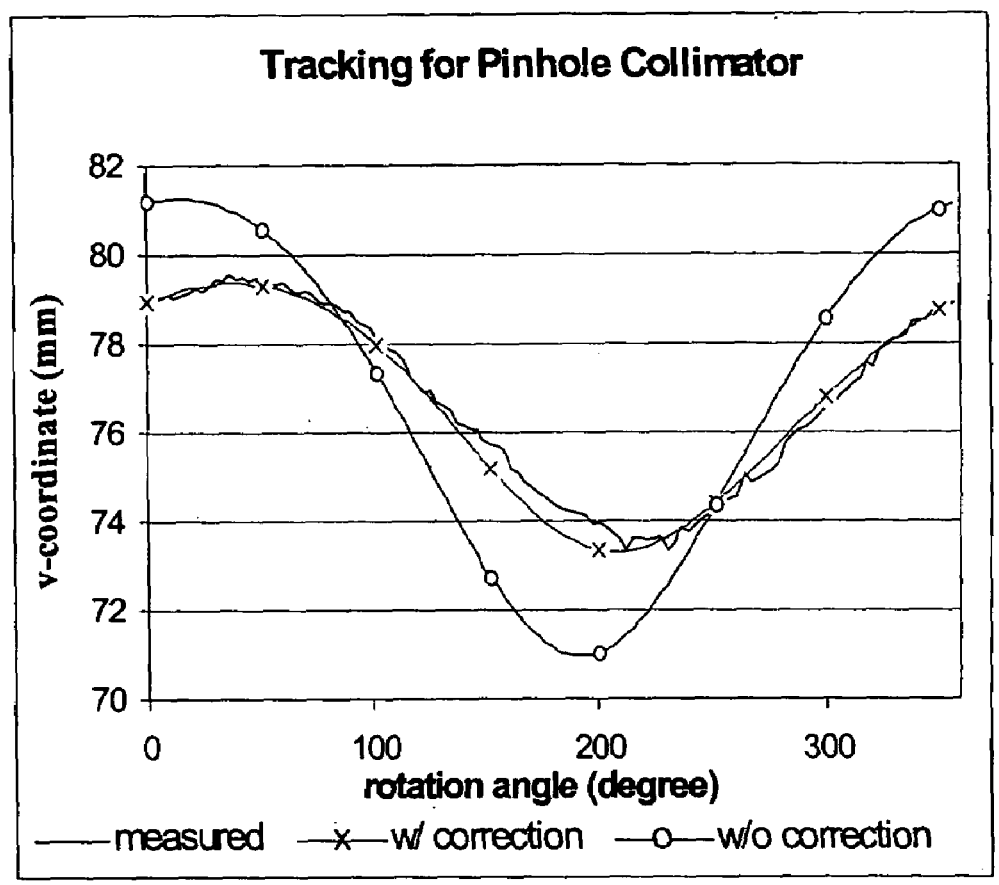
FIG. 15 is a graph showing the measured and predicted v-coordinates for 1 of the 3 point sources in the calibration of a pinhole detector.
Figure 16:
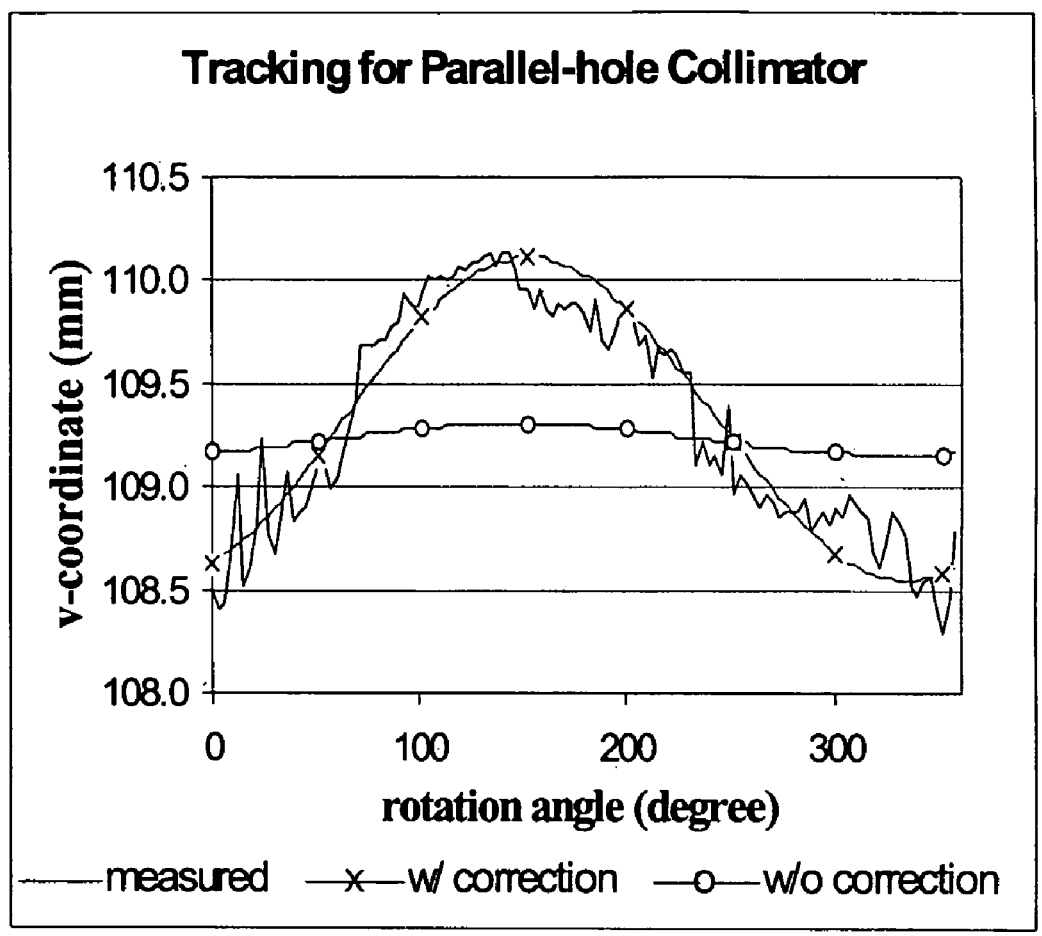
FIG. 16 is a graph showing the measured and predicted v-coordinates for a detector fitted with a parallel hole collimator.

The effectiveness of the axial correction function for geometry calibration is shown in FIGS. 15 and 16. FIG. 15 is a graph showing the measured and predicted v coordinates for 1 of the 3 point sources used in-calibration of a pinhole collimator. With the correction function described herein the predicted paths closely track the measured paths. Without correction, prediction error may exceed 2 mm in some locations in the v direction. Negligible prediction errors were observed in the u direction. FIG. 16 shows that similar results were obtained for a detector fitted with a parallel-hole collimator. The observed error for the detector with a parallel-hole collimator was small but detectable. For the pinhole camera, a small unwanted axial displacement was magnified 2-3 times. A mere ¾ mm axial displacement can thus result in a projection error of 2-3 mm. This correction is very important for small imaging applications.

There has thus been described a method for simultaneous calibration of a dual-headed imaging system that shows improved fitting using the extended calibration method described herein.

As the invention has been described, it will be apparent to those skilled in the art that the same may be varied in many ways not previously described herein without departing from the intended spirit and scope of the invention, and any and all such modifications are intended to be included within the scope of the appended claims.

What is claimed is:

1. In a method for obtaining high resolution dynamic images of conscious living subjects comprising the simultaneous acquisition of multiple images by a plurality of gantry mounted, high sensitivity and high spatial resolution dynamic pinhole or parallel-hole collimator imagers that may be subject to unwanted movement due to gantry flexing or axial motion that affects the spatial resolution of the multiple images, the improvement comprising:

A) calibrating two or more of the imagers to the same coordinate system; and

B) functionally correcting the acquired multiple images for unwanted detector movement due to gantry flexing and axial motion to obtain corrected spatial resolution of the acquired multiple images through the iterative application of the following equation:

$$\Delta v \approx f/d(d\,\tan(\Delta\phi)) = f\tan(\Delta\phi)$$

wherein v is one of two orthogonal coordinates defined in the plane of the detector, d is the distance from the axis of rotation to the pinhole and $\Delta\phi$ is the rocking angle through which the detector moves during rotation about a target.

2. The method of claim 1 wherein the functional correction for axial motion is obtained through the iterative application of the following equations:

$$v = \frac{-f(m_v - z_0''' - g_{z'''})}{d - y_0''' - g_{y'''}} + m_v + e_v$$

$$u = \frac{-f(m_u - x_0''' - g_{x'''})}{d - y_0''' - g_{y'''}} + m_u + e_u$$

wherein u and v are coordinates in the projection space or coordinates of detectors; m and e are mechanical and electronic shifts; and the triple primed coordinates ($x_0'''$, $y_0'''$, $z_0'''$) denote transformations without axial motion term g.

3. The method of claim 2 wherein functional correction for unwanted detector movement due to gantry flexing is obtained through the iterative application of the following equation:

$$\Delta v \approx f/d(d\,\tan(\Delta\phi)) = f\tan(\Delta\phi)$$

wherein v is one of two orthogonal coordinates defined in the plane of the detector, d is the distance from the axis of rotation to the pinhole and $\Delta\phi$ is the rocking angle through which the detector moves during rotation about a target.

4. In a method for obtaining high resolution dynamic images of conscious living subjects comprising the simultaneous acquisition of multiple images by a plurality of gantry mounted, high sensitivity and high spatial resolution dynamic pinhole or parallel-hole collimator imagers that may be subject to unwanted movement due to gantry flexing or axial motion that affects the spatial resolution of the multiple images, the improvement comprising:

A) calibrating two or more of the imagers to the same coordinate system;

B) functionally correcting the acquired multiple images for unwanted detector movement due to gantry flexing through the iterative application of the following equation:

$$\Delta v \approx f/d(d\,\tan(\Delta\phi)) = f\tan(\Delta\phi)$$

wherein v is one of two orthogonal coordinates defined in the plane of the detector, d is the distance from the axis of rotation to the pinhole and $\Delta\phi$ is the rocking angle through which the detector moves during rotation about a target and axial motion; and correction for axial motion is obtained through the iterative application of the following equations:

$$v = \frac{-f(m_v - z_0''' - g_{z'''})}{d - y_0''' - g_{y'''}} + m_v + e_v$$

$$u = \frac{-f(m_u - x_0''' - g_{x'''})}{d - y_0''' - g_{y'''}} + m_u + e_u$$

wherein u and v are coordinates in the projection space or coordinates of detectors; m and e are mechanical and electronic shifts; and the triple primed coordinates ($x_0'''$, $y_0'''$, $z_0'''$) denote transformations without axial motion term g to obtain corrected spatial resolution of the acquired multiple images.

* * * * *